(12) United States Patent
Dervaes

(10) Patent No.: US 9,625,434 B2
(45) Date of Patent: Apr. 18, 2017

(54) DRIPLESS, PERMANENT SEALING ASSEMBLY FOR CONTAINER

(71) Applicant: Hach Company, Loveland, CO (US)

(72) Inventor: Nelson Dervaes, Fort Collins, CO (US)

(73) Assignee: Hach Company, Loveland, CO (US)

( * ) Notice: Subject to any disclaimer, the term of this patent is extended or adjusted under 35 U.S.C. 154(b) by 627 days.

(21) Appl. No.: 13/899,127

(22) Filed: May 21, 2013

(65) Prior Publication Data
US 2014/0345368 A1    Nov. 27, 2014

(51) Int. Cl.
| | |
|---|---|
| *B01L 3/00* | (2006.01) |
| *G01N 33/18* | (2006.01) |
| *B05B 15/00* | (2006.01) |
| *B65B 3/00* | (2006.01) |
| *B65D 47/06* | (2006.01) |
| *B67D 7/02* | (2010.01) |

(52) U.S. Cl.
CPC .............. *G01N 33/18* (2013.01); *B01L 3/523* (2013.01); *B05B 15/005* (2013.01); *B65B 3/00* (2013.01); *B65D 47/06* (2013.01); *B01L 2200/026* (2013.01); *B01L 2200/0689* (2013.01); *B01L 2200/141* (2013.01); *B01L 2300/042* (2013.01); *B67D 7/0288* (2013.01)

(58) Field of Classification Search
CPC ...... A61J 1/2031; A61J 1/1418; A61J 1/1481; A61J 1/1487; B01L 2200/141; B01L 2300/042; B01L 3/523; B65D 47/06; B67D 7/0288

See application file for complete search history.

(56) References Cited

U.S. PATENT DOCUMENTS

| | | | | |
|---|---|---|---|---|
| 1,219,937 A | * | 3/1917 | Green | ............................ 604/403 |
| 2,461,620 A | * | 2/1949 | Wright | ................. B65D 47/283 |
| | | | | 215/311 |
| 2,815,879 A | * | 12/1957 | Hermes | ........................ 215/12.1 |

(Continued)

FOREIGN PATENT DOCUMENTS

| | | |
|---|---|---|
| CN | 102458341 A | 5/2012 |
| DE | 19838685 C1 | 11/1999 |

(Continued)

OTHER PUBLICATIONS

"Series 5000 Silica Analyzer, Model 6000 Instrument Manual", Hach Company, Nov. 2004.*

(Continued)

*Primary Examiner* — David A Rogers
(74) *Attorney, Agent, or Firm* — Ference & Associates LLC

(57) ABSTRACT

An embodiment provides a permanent sealing assembly for a container, such as a reagent bottle. The permanent sealing assembly allows for drip-less reagent container exchange for liquid analysis instruments. The permanent sealing assembly may be integrated into a container, such as a reagent bottle, and provides an outflow tube that extends into the container. The permanent sealing assembly and the outflow tube thereof remain in the container such that, on an exchange of regent containers, a removable cap assembly of the liquid analysis instrument may be affixed to a new container of reagent without the risk of reagent from the old container contacting the surroundings. Other aspects are described and claimed.

9 Claims, 10 Drawing Sheets

(56) References Cited

U.S. PATENT DOCUMENTS

| | | | |
|---|---|---|---|
| 3,313,439 A * | 4/1967 | Robinson | 215/247 |
| 4,095,726 A * | 6/1978 | Hechler, IV | A01M 7/0046 |
| | | | 222/175 |
| 4,230,112 A * | 10/1980 | Smith | 604/403 |
| 4,238,040 A * | 12/1980 | Fitzpatrick | A61J 9/001 |
| | | | 215/11.3 |
| 4,303,071 A * | 12/1981 | Smith | 604/403 |
| 4,452,268 A * | 6/1984 | Icking | A01J 7/022 |
| | | | 119/14.18 |
| 4,852,781 A * | 8/1989 | Shurnick et al. | 224/148.2 |
| 4,994,076 A * | 2/1991 | Guss | A61J 9/00 |
| | | | 215/11.1 |
| 5,048,705 A * | 9/1991 | Lynd et al. | 215/388 |
| D324,824 S * | 3/1992 | Hansen | D9/436 |
| D327,848 S * | 7/1992 | Hanover | D9/436 |
| 5,174,460 A * | 12/1992 | Minnette | 215/335 |
| 5,337,918 A * | 8/1994 | Wang | 220/708 |
| 5,406,991 A * | 4/1995 | Rathenberg et al. | 141/18 |
| 5,509,551 A * | 4/1996 | Terrell, II | 215/229 |
| 5,598,939 A * | 2/1997 | Watson et al. | 215/307 |
| 5,957,328 A * | 9/1999 | Osgar | B67D 7/0294 |
| | | | 222/1 |
| 6,290,090 B1 * | 9/2001 | Essebaggers | B65D 47/248 |
| | | | 220/705 |
| 7,793,801 B2 * | 9/2010 | Drummond | 222/179 |
| 8,171,963 B2 * | 5/2012 | Sonnier | 141/27 |
| 8,281,961 B2 * | 10/2012 | Martin | 222/482 |
| 8,763,829 B2 * | 7/2014 | Madaus | 215/44 |
| 9,296,212 B2 * | 3/2016 | Gonzalez | B41J 2/17509 |
| 2002/0148806 A1 * | 10/2002 | Cheng | 215/388 |
| 2006/0186076 A1 | 8/2006 | Shiloni | |
| 2007/0235105 A1 * | 10/2007 | Ramsey | A45F 3/16 |
| | | | 141/323 |
| 2008/0283143 A1 * | 11/2008 | McKibbin et al. | 141/27 |
| 2010/0102094 A1 | 4/2010 | Rice et al. | |
| 2010/0112815 A1 * | 5/2010 | O'Dougherty | B67D 7/0261 |
| | | | 438/689 |
| 2012/0067459 A1 | 3/2012 | Kunishige et al. | |

FOREIGN PATENT DOCUMENTS

| | | | | |
|---|---|---|---|---|
| GB | 2197303 A | 5/1988 | | |
| WO | 2007091887 A1 | 8/2007 | | |
| ZA | WO 2010004486 A1 * | 1/2010 | | B65D 47/0838 |

OTHER PUBLICATIONS

Greenmaker Industries, Closed Loop Dispensing Systems, Aug. 4, 2012, available on the internet at <https://web.archive.org/web/20120804091543/http://www.greendepot.com/greendepot/assets/images/docs/BlendMateClosedLoop_TDS.pdf>.*

International Searching Authority (EPO), Search Report for International Application PCT/US2014/038772, Sep. 11, 2014, 5 pages, The Hague, Netherlands.

* cited by examiner

DRIPLESS, PERMANENT SEALING ASSEMBLY FOR CONTAINER

BACKGROUND

Liquid analysis instruments, e.g., water process instruments such as the series 5500 silica analyzer or spectrophotometer instruments, each available from Hach Company of Loveland, Colo., are used to analyze liquids. For example, such water analysis instruments find use in determining purity of water used in industrial applications that demand pure water.

These analysis instruments use bottled reagents to perform chemical analyses on a sample. The bottled reagents are consumed by the analysis instrument and must be replaced with new bottles, e.g., every 1-3 months. In the prior art an intake or outflow tube extends down from the bottle cap, which is attached to the analysis instrument via tubing, into the solution in the reagent bottle. The tubing that extends into the reagent bottle (and into the reagents) is affixed to the cap. On replacement of a bottle of reagent, the cap is removed from the reagent bottle and a new reagent bottle is opened and has the cap/tubing affixed to it. This allows the analysis instrument to continue processing using the bottled reagent in question. A common problem that arises during the changeover is that dripping reagent may spill on clothes, the analysis instrument, and in addition contaminants may be introduced to the new reagent by contamination of the exterior of the reagent line that goes inside the bottle. Therefore, better reagent bottle interface designs are desirable.

BRIEF SUMMARY

In summary, an embodiment provides a removable cap assembly comprising: an outer portion that attaches to an orifice of a container; a connecting portion that, when the outer portion of the removable cap assembly is secured to the orifice of the bottle, contacts and seals with an outflow tube portion of a permanent sealing assembly of the container; an inflow tube that provides inflow of a gas to provide positive pressure to the container interior; and an outflow tube extending from the connecting portion that provides outflow of contents of the container via fluid communication with the outflow tube of the permanent sealing assembly of the container.

Another embodiment provides a system, comprising: a liquid analysis instrument comprising a microprocessor in electrical communication with valves and a gas manifold; and a removable cap assembly comprising: an outer portion that attaches to an orifice of a container; a connecting portion that, when the outer portion of the removable cap assembly is secured to the orifice of the container, contacts and seals with an outflow tube portion of a permanent sealing assembly of the container; an inflow tube that provides inflow of a gas from the liquid analysis instrument to provide positive pressure to the container interior; and an outflow tube extending from the permanent connecting portion that provides outflow of contents of the container to the liquid analysis instrument via fluid communication with the outflow tube of the permanent sealing assembly of the container.

Another embodiment provides a container having an integral permanent sealing assembly, comprising: a container orifice; a permanent sealing assembly fitted to the orifice; and an outflow tube portion extending from the permanent sealing assembly; the permanent sealing assembly having therein one or more vent apertures; and the permanent sealing assembly having a connecting portion that interfaces with a connecting portion of a removable cap assembly.

A further embodiment provides a permanent sealing assembly, comprising: an outer periphery fitted to the shape of an orifice of a container; one or more vent apertures disposed within the permanent sealing assembly, the one or more vent apertures allowing an inflow of pressurized gas into an interior of the container; a port that interfaces with a connecting portion of a removable cap assembly, the port of the permanent sealing assembly providing fluid outflow of contents of the container to the connecting portion of the removable cap assembly when the container is pressurized; and an outflow tube portion extending from the port of the permanent sealing assembly.

A still further aspect provides a method, comprising: inserting one or more filling tubes into a container; dispensing one or more reagents into the container; and affixing a permanent sealing assembly to an orifice of the container, the permanent sealing assembly comprising: an outer periphery fitted to the shape of an orifice of the container; one or more vent apertures disposed within the permanent sealing assembly, the one or more vent apertures allowing an inflow of pressurized gas into an interior of the container; a port that interfaces with a connecting portion of a removable cap assembly, the port of the permanent sealing assembly providing fluid outflow of contents of the container to the connecting portion of the removable cap assembly when the container is pressurized; and an outflow tube portion extending from the port of the permanent sealing assembly.

The foregoing is a summary and thus may contain simplifications, generalizations, and omissions of detail; consequently, those skilled in the art will appreciate that the summary is illustrative only and is not intended to be in any way limiting.

For a better understanding of the embodiments, together with other and further features and advantages thereof, reference is made to the following description, taken in conjunction with the accompanying drawings. The scope of the invention will be pointed out in the appended claims.

DETAILED DESCRIPTION

It will be readily understood that the components of the embodiments, as generally described and illustrated in the figures herein, may be arranged and designed in a wide variety of different configurations in addition to the described example embodiments. Thus, the following more detailed description of the example embodiments, as represented in the figures, is not intended to limit the scope of the embodiments, as claimed, but is merely representative of example embodiments.

Reference throughout this specification to "one embodiment" or "an embodiment" (or the like) means that a particular feature, structure, or characteristic described in connection with the embodiment is included in at least one embodiment. Thus, appearances of the phrases "in one embodiment" or "in an embodiment" or the like in various places throughout this specification are not necessarily all referring to the same embodiment.

Furthermore, the described features, structures, or characteristics may be combined in any suitable manner in one or more embodiments. In the following description, numerous specific details are provided to give a thorough understanding of embodiments. One skilled in the relevant art will recognize, however, that the various embodiments can be practiced without one or more of the specific details, or with other methods, components, materials, et cetera. In other instances, well-known structures, materials, or operations are not shown or described in detail. The following description is intended only by way of example, and simply illustrates certain example embodiments.

The term "permanent" is used to describe a container aperture or orifice seal that is permanent during the intended lifetime of the reagent bottle or container. The seal may in fact be removable, but its intended use is to remain in the aperture or orifice at all times during reagent usage.

The term "bottle" is used as a representative example to describe a container for liquid to which a cap may be affixed. The "bottle" may be formed from a rigid material, e.g., glass or plastic or other polymer, or a flexible material, e.g., a bag or pouch. Therefore, throughout this description "container" may be substituted for "bottle" unless specifically noted otherwise.

The phrase "water analysis instrument" is used throughout as a representative example to describe a liquid or fluid analysis instrument. Therefore occurrences of this phrase throughout the description include more generally "analysis instrument(s)" and thus "analysis instrument" may be substituted for "water analysis instrument" throughout this description unless specifically noted otherwise.

Figure 1B:
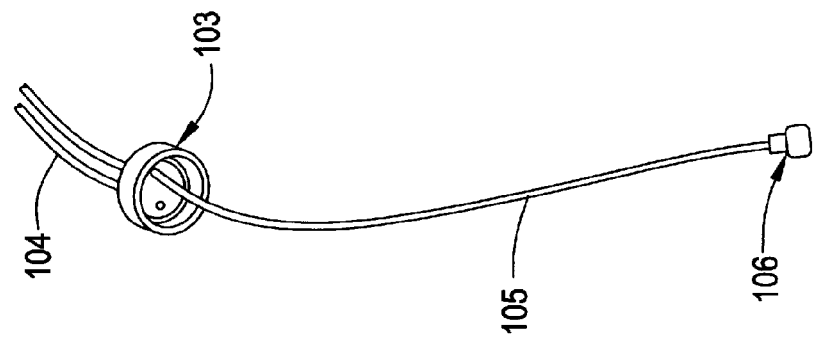
FIG. 1 (A-B) illustrates an example of a conventional reagent bottle and cap assembly.
Figure 1A:
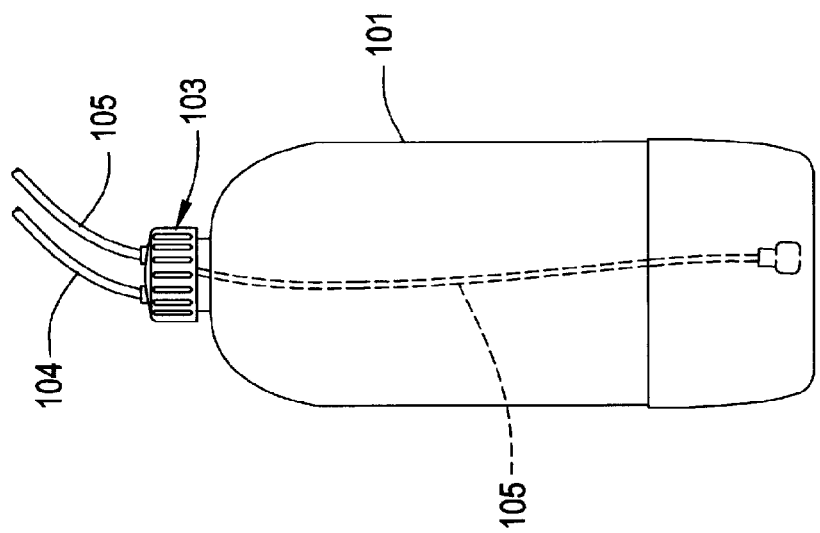

Referring to FIG. 1A, in the prior art, a reagent bottle is simply a bottle without having any additional components internal thereto. Therefore, when a reagent bottle is to be replaced, manually, the outflow tube 105 (providing outflow from the reagent bottle to a liquid analysis instrument, not shown) of the cap assembly 103 extends from the cap assembly 103 into the interior of the reagent bottle 101. The cap assembly 103 also includes an inflow tube 104 that provides positive pressure to the reagent bottle 101 (to permit outflow of reagent to the liquid analysis instrument via the outflow tube 105).

As appreciated from FIG. 1B, the cap assembly 103 (attached to the liquid analysis instrument via tubing 104, 105) includes a portion of the outflow tube 105 which extends down into the reagent bottle 101. Therefore, when a prior art reagent bottle 101 is replaced, the outflow tubing 105 that extends into the interior of the reagent bottle 101 is typically wet with reagent, which drips from the outflow tubing 105. This reagent is often caustic (e.g., sulfuric acid) or otherwise a substance (e.g., a dye) that is not to be contacted with surrounding materials. That is, many of the reagents contained in the reagent bottles may have negative impacts on the surrounding materials if contacted (e.g., stain clothing or other materials that may come into contact with the reagent). Thus, the reagent dripping from the outflow tubing 105 creates an undesirable situation in which the worker performing the reagent replacement procedure must consciously avoid dripping reagent.

Moreover, if the cap assembly 103 is laid down in the process of refilling, the cap assembly 103 and/or tubing, e.g., outflow tube/tubing 105, is prone to pick up contaminants from the surrounding environment. This may cause contamination of the liquid analysis instrument or affect the quality of measurements by contaminating the reagent in the new reagent bottle 101 (once cap assembly 103 is fitted thereon). Such contamination may reduce the accuracy of the liquid analysis instrument when the cap assembly 103 is inserted into a new reagent bottle 101.

An embodiment provides a permanent sealing assembly for a container, such as a reagent bottle. The permanent sealing assembly allows for drip-less reagent container exchange for liquid analysis instruments. The permanent sealing assembly may be integrated into a container, such as a reagent bottle, and provides an outflow tube that extends into the container. The permanent sealing assembly and the outflow tube thereof remain in the container such that, on an exchange of reagent containers, a removable cap assembly of the liquid analysis instrument may be affixed to a new container of reagent without the risk of reagent from the old container contacting the surroundings.

Figure 2C:
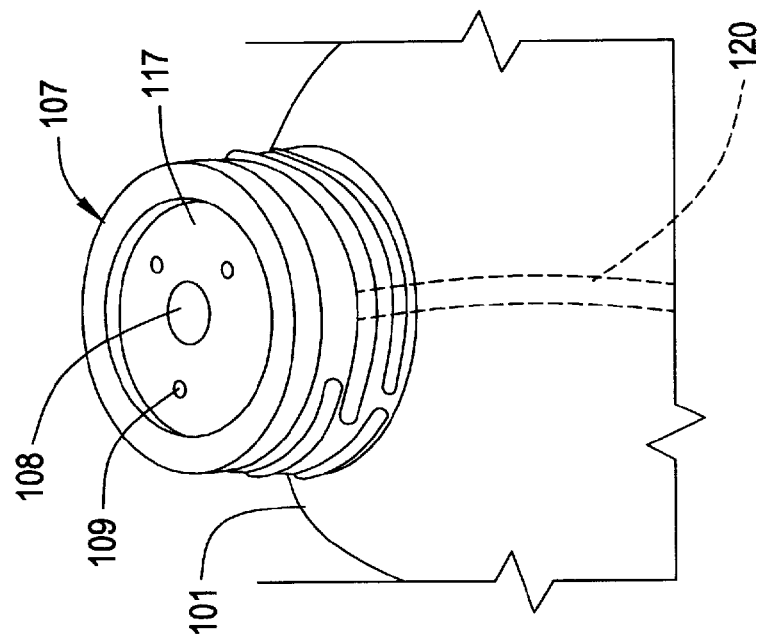
FIG. 2 (A-C) illustrates an example of a sealing assembly and tube portion thereof for a reagent bottle.
Figure 2B:
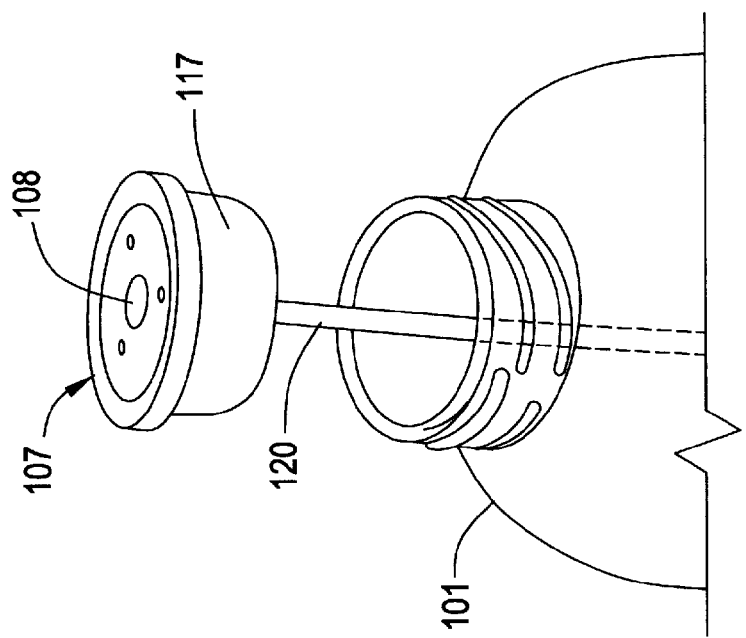
Figure 2A:
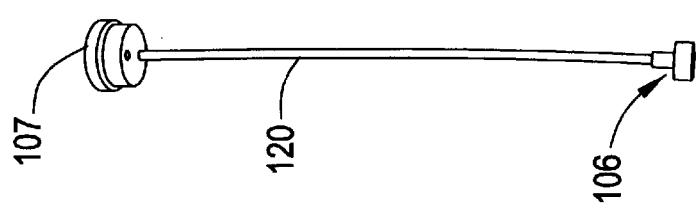

Accordingly, referring to FIG. 2 (A-C), an embodiment provides a permanent sealing assembly 107 that is formed in or affixed to the reagent bottle 101 at an orifice of the reagent bottle 101. The permanent sealing assembly 107 may for example fit into the orifice of the reagent bottle 101 in the form of a stopper, although other configurations are possible. If the permanent sealing assembly 107 takes the form of a stopper, it may be permanently affixed into the orifice of the reagent bottle 101, e.g., via ultrasonic welding. The permanent sealing assembly 107 may comprise a one-time use material, e.g., a material such as a septum that is to be single use only. Alternatively, a removable sealing assembly (not illustrated) may be employed, e.g., via a snap-on or screw-on arrangement.

The permanent sealing assembly 107 comprises an elastomeric stopper body 117 that includes or otherwise interfaces with a tube portion 120 that serves as an outflow tube, allowing reagent contained within the reagent bottle 101 to flow out of the bottle and into a liquid analysis instrument 110. The reagent flows out via the tube portion 120 and a port 108 that connects to an outflow tube 121 of a (removable) cap assembly 111 (illustrated in, e.g., FIG. 6). The port 108 acts as an interface to connect the outflow tube portion 120 to the outflow tube portion 121. In one example embodiment, described further in detail below, the port 108 may take the form of a depression that sealingly interfaces with a nipple 116 of a removable cap assembly 111.

The permanent sealing assembly 107 further includes one or more vent apertures 109 that allow gas (e.g., air) inflow to pressurize the interior of the reagent bottle 101, as for example provided by an inflow tube 104 of the removable cap assembly 111. The vent aperture(s) 109 may be formed integrally to the permanent sealing assembly 107, e.g., via a molding process, may be formed in a filling operation or use operation (e.g., via punching hole(s) in the permanent sealing assembly 107 with a filling tube or with the removable cap assembly 111, etc.) or a suitable combination of the foregoing. The permanent sealing assembly 107 may include a mesh or other material layer (e.g., manually removable material such as a polymer or wax) that acts to cover or preclude or reduce fluid outflow and/or air inflow via the vent aperture(s) 109, e.g., during shipping. Manually removable foil-backed polymeric seals may also be used during shipping to create an additional layer of leak protection.

The aperture(s) 109 in the permanent sealing assembly 107 may be purposely fashioned as multiple vent holes with small diameters, or alternatively the vent holes may be sealed with a gas-permeable but liquid impermeable material such as GORETEX material. This helps to ensure that air may easily pass through the aperture(s) 109, but liquids will have more difficulty passing there-through because of their viscosity and surface tension. This benefits the user in that a container 101 that is knocked over (e.g., during use) will leak very little liquid compared to a conventional container (e.g., bottle 101 of FIG. 1A).

The aperture(s) 109 may be supplemented or replaced by a membrane, mesh, or porous material (e.g., ceramic, plastic, etc.) that allows air to pass through but blocks liquid passage. Another option is to include a one-way valve in the permanent sealing assembly 107 that allows air to travel through from the outside, but blocks liquid from moving from the inside to the outside (except as desired, e.g., through the outflow tubes 120, 121 (as described further herein)).

At a terminal portion of the tube portion 120 a filter assembly 106 may be provided to ensure fluid flow when the tube portion 120 is included with the reagent bottle 101, e.g., via forming a passageway for fluid flow through the filter assembly 106. The filter assembly 106 may include a filter screen that acts to preclude or reduce particulate (e.g., contained within a liquid reagent) from flowing out of the reagent bottle 101 during use.

Figure 3:
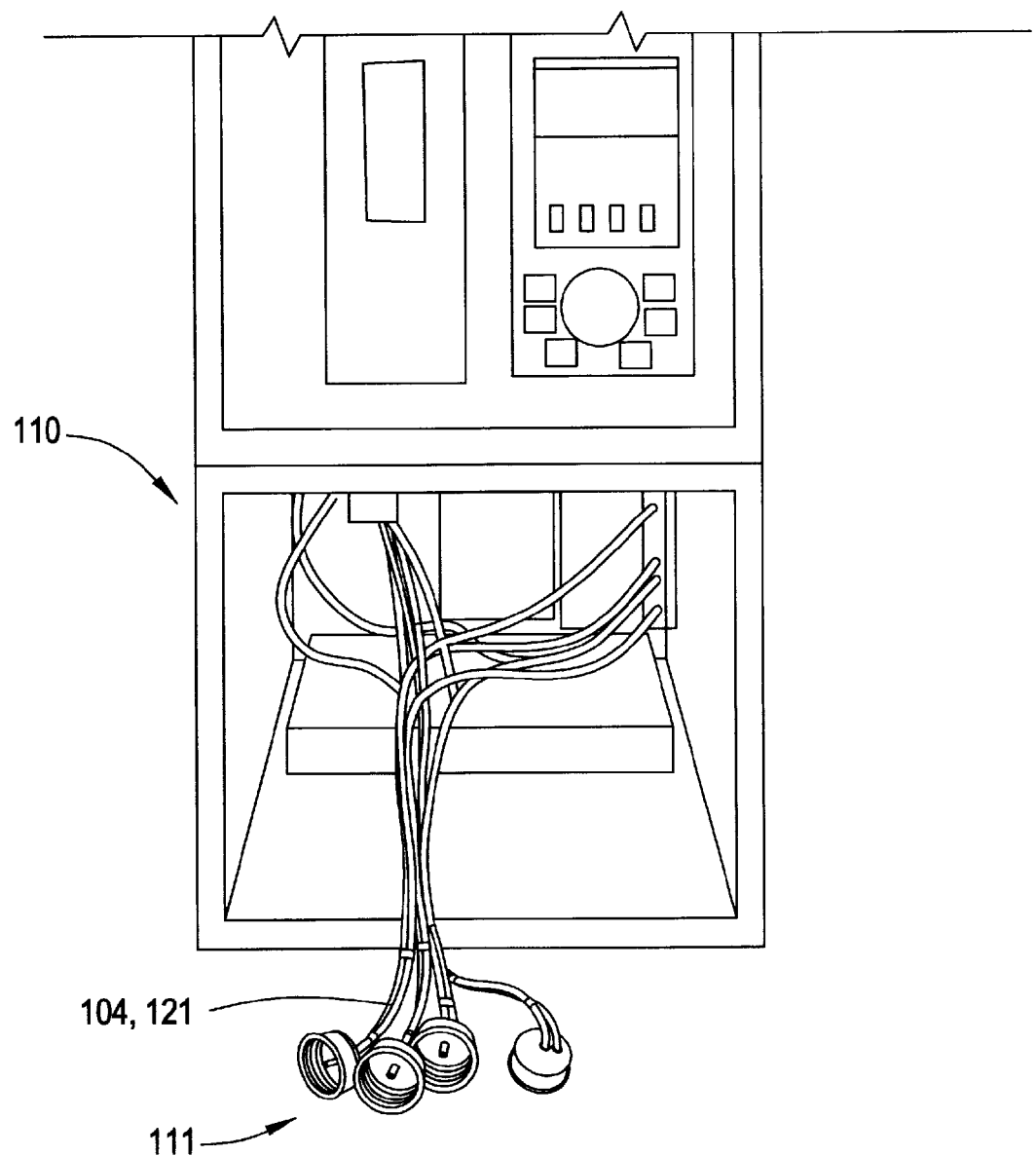
FIG. 3 illustrates an example of a liquid analysis instrument with tubing and removable cap assemblies attached thereto.

Turning to FIG. 3, an exemplary liquid analysis instrument 110, a water analysis instrument, is illustrated along with a removable cap assembly 111. The removable cap assembly 111 is attached to the water analysis instrument 110 via tubing, e.g., inflow tube 104 and outflow tube 121. Inflow tube 104 is provided in the removable cap assembly 111 such that it terminates within the removable cap assembly 111 and provides gas inflow to the permanent sealing assembly 107 and via vent aperture(s) 109 to the interior of the reagent bottle 101. The inflow tube 104 may terminate prior to contacting permanent sealing assembly 107, e.g., at the underside of the removable cap assembly 111. Thus, the inflow tube 104 need not be directly aligned with the vent aperture(s) 109 of the permanent sealing assembly 107, as clearance between a terminating portion of the inflow tube 104 and the permanent sealing assembly's 107 upper surface allows gas (e.g., air) to enter vent apertures 109 and pressurize the reagent bottle 101. A gas manifold of the water analysis instrument 110 provides gas pressure to inflow tube 104. A programmed microprocessor included in the water analysis instrument 110 controls gas valves (not shown) that direct and re-direct gas pressure to the manifold and reagent bottle(s) 101, and also provide a source of venting to atmosphere when the access door is opened or when programmed to vent.

Figure 4:
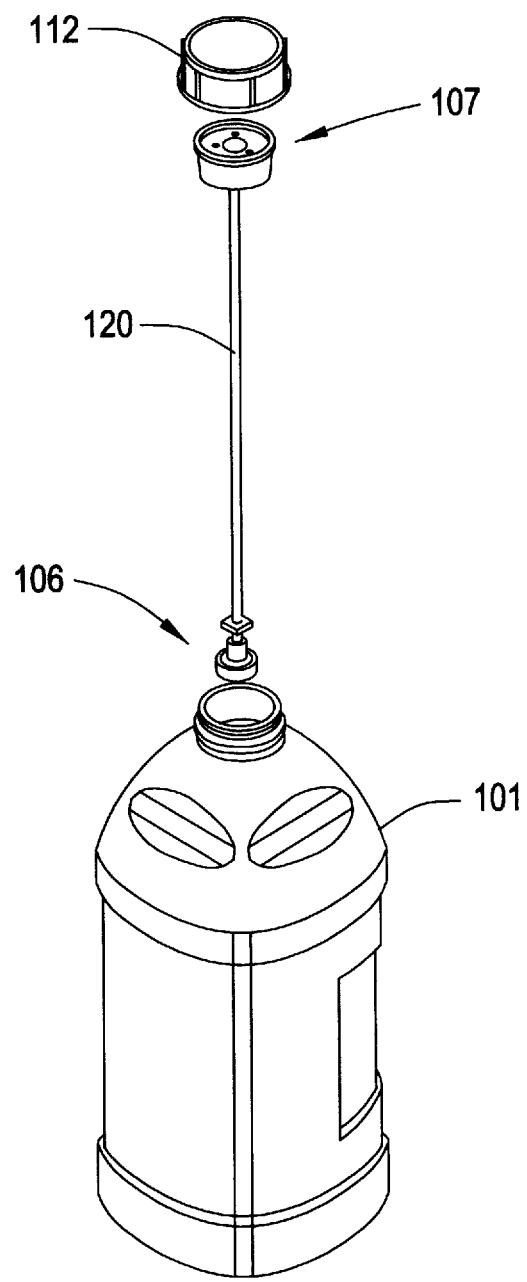
FIG. 4 illustrates an exploded view of an example sealing assembly and tube portion thereof for a reagent bottle.

In FIG. 4 an exploded view of an example reagent bottle 101 is provided. The permanent sealing assembly 107 sits beneath a temporary cap 112 (e.g., that may be removed after shipping when the reagent bottle 101 is to be opened and used). The permanent sealing assembly 107 again includes a tube portion 120 that will extend into the interior of the reagent bottle 101. At a terminal portion of the tube portion 120 a filter assembly 106 may be provided, again such that the terminal portion of the tube portion 120 allows for some clearance between its end surface (or a portion thereof) and the bottom interior surface of the reagent bottle 101. This allows reagent to flow up the tube portion 120 and out of the reagent bottle 101 to the water analysis instrument 110 via outflow tube 121 of the removable cap assembly 111.

Figure 5B:
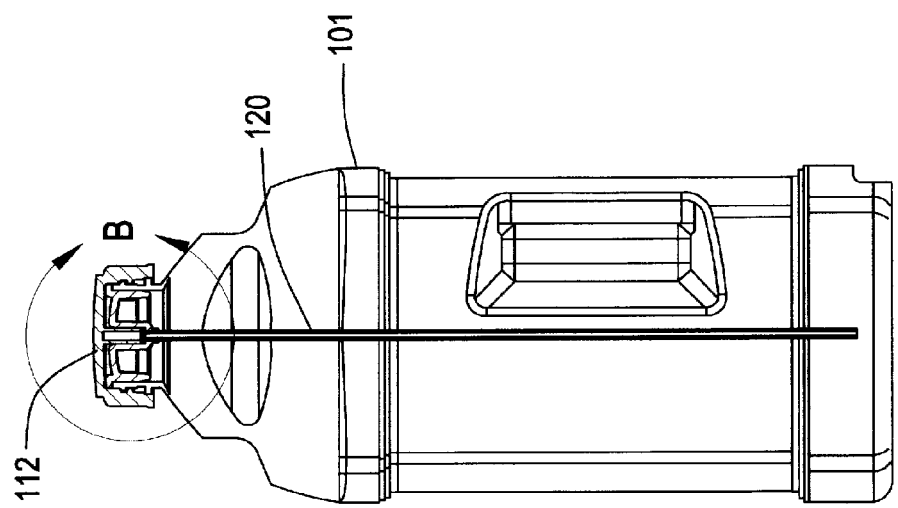
FIG. 5B illustrates a cross section of FIG. 5A.
Figure 5A:
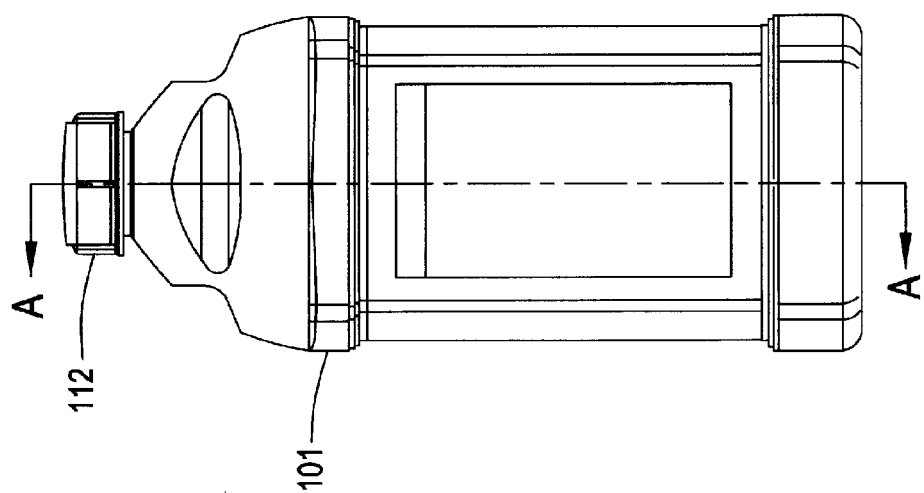
FIG. 5A illustrates an example sealing assembly for a reagent bottle.

FIGS. 5A and 5B illustrate side and cross sectional views (along section A-A) of an example reagent bottle 101, respectively. As can be appreciated from these example illustrations, the temporary cap 112 and the permanent sealing assembly 107 coordinate to ensure that the reagent bottle 101 is sealed, e.g., prior to use. The tube portion 120 of the permanent sealing assembly 107 extends downward into the interior of the reagent bottle 101 when the reagent bottle 101 is assembled.

Figure 5C:
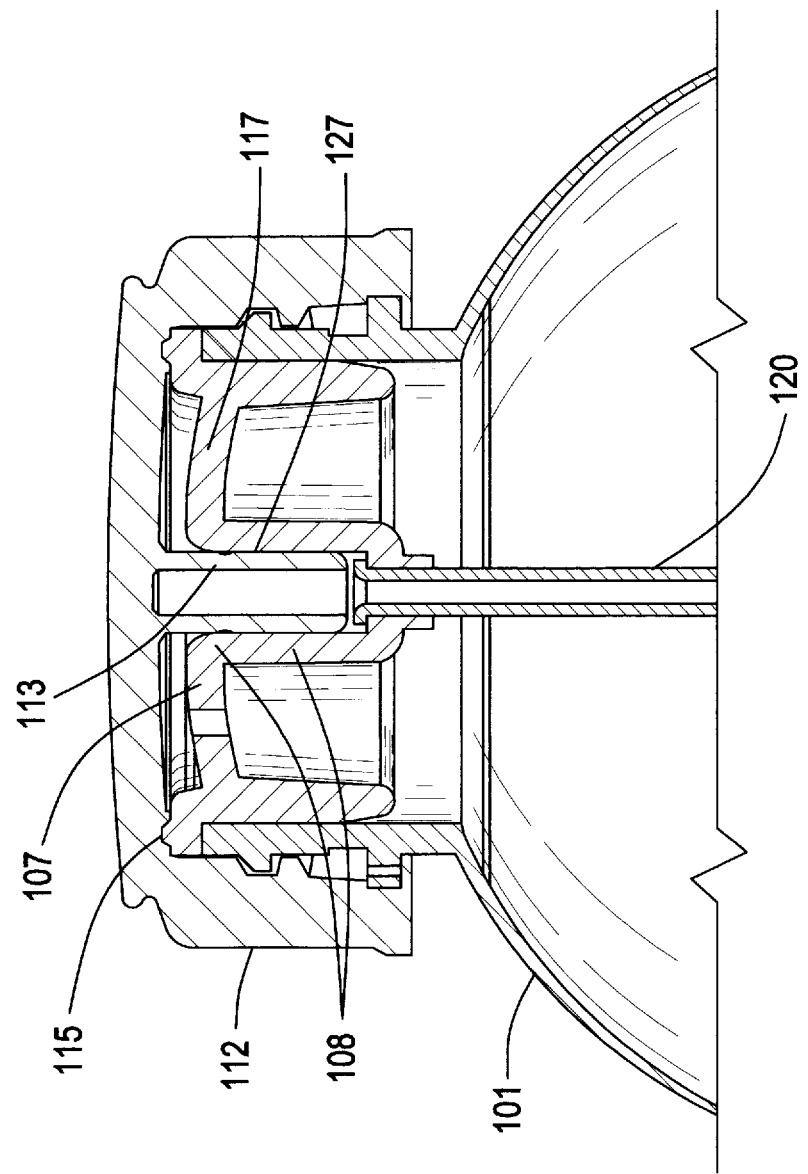
FIG. 5C illustrates an enlarged view of area B of FIG. 5B.

FIG. 5C illustrates a cross sectional view of the temporary cap 112, the permanent sealing assembly 107, the tube portion 120 of the permanent sealing assembly 107, and the reagent bottle 101. As illustrated threading may be used to secure the temporary cap 112 and to corresponding threading of an orifice of the reagent bottle 101 such that the reagent bottle 101 is sealed by contact between permanent sealing assembly 107, e.g., at sealing bead 115, and the temporary cap 112. A similar threading mechanism may be utilized to secure the removable cap assembly 111 to the orifice of the reagent bottle 101.

In this regard the temporary cap 112 or the removable cap assembly 111 may include an outer portion for connecting to a container orifice. The outer portion may include threading that is complimentary to threading of a container. Again, other securing mechanisms may adhere outer portions of cap(s) to bottles or containers, such as snap-on arrangements, one time use arrangements, or the like.

The temporary cap 112 may include an element such as sealing nipple 113 that interfaces with the permanent sealing assembly 107, e.g., a corresponding depression corresponding to the port 108 of the permanent sealing assembly 107. The port 108 may additionally include a sealing bead 127 that provides sealing contact with the nipple 113 on insertion thereof. In a similar way, the removable cap assembly 111 (attached to the water analysis instrument 110) may include a hollow nipple 116 that inserts into the permanent sealing assembly 107, but has a hollow lumen to provide for sealing contact and fluid flow, as further described herein.

Figure 6:
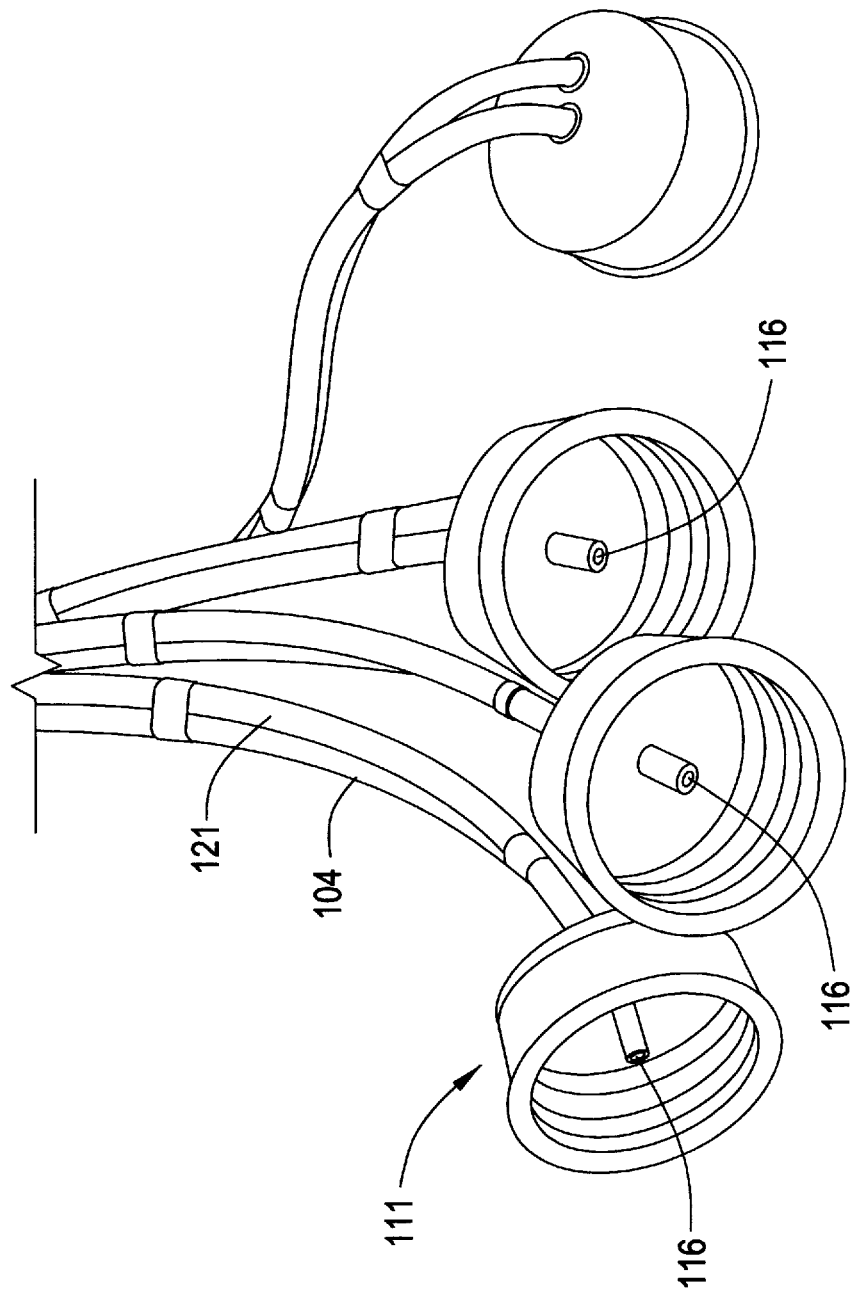
FIG. 6 illustrates example removable cap assemblies having tubing attached thereto.

In FIG. 6, removable cap assemblies 111 are illustrated along with corresponding tubing, e.g., inflow tube 104 and outflow tube 121. Here, a connecting portion of the removable cap assembly 111 takes the form of a hollow nipple 116 that extends from the removable cap assembly 111, similar to the element 113 of the temporary cap 112. However, the hollow nipple 116 of the removable cap assembly 111 includes a fluid communication mechanism, e.g., a hollow center or lumen, such that reagent may flow out of the reagent bottle 101 (not illustrated in FIG. 6) and into the water analysis instrument 110, e.g., via outflow tube 121, when the reagent bottle 101 is pressurized.

As can be appreciated, the removable cap assembly 111 may include threading for removable connection with a reagent bottle 101 much in the same way temporary cap 112 includes threading. Moreover, the removable cap assembly 111 also contacts the permanent sealing assembly 107 at least at the outer periphery of the underside of the removable cap assembly 111 (corresponding to contact points and sealing bead 115 with the outer margin of the reagent bottle 101 orifice) such that the reagent bottle may be pressurized by inflow of gas via inflow tube 104 when the removable cap assembly 111 is secured to the reagent bottle 101.

As illustrated in FIG. 6, the inflow tube 104 does not need to extend beyond the inner surface of the removable cap assembly 111. This permits, along with clearance between the underside of the removable cap assembly 111 and the upper surface of the permanent sealing assembly 107, the inflow of gas from inflow tube 104 through vent aperture(s) 109 in the permanent sealing assembly 107, which in turn allows the gas to pressurize the reagent bottle 101 interior, even if the inflow tube 104 is not aligned with the vent aperture(s) 109, or one or more vents is blocked.

Figure 7:
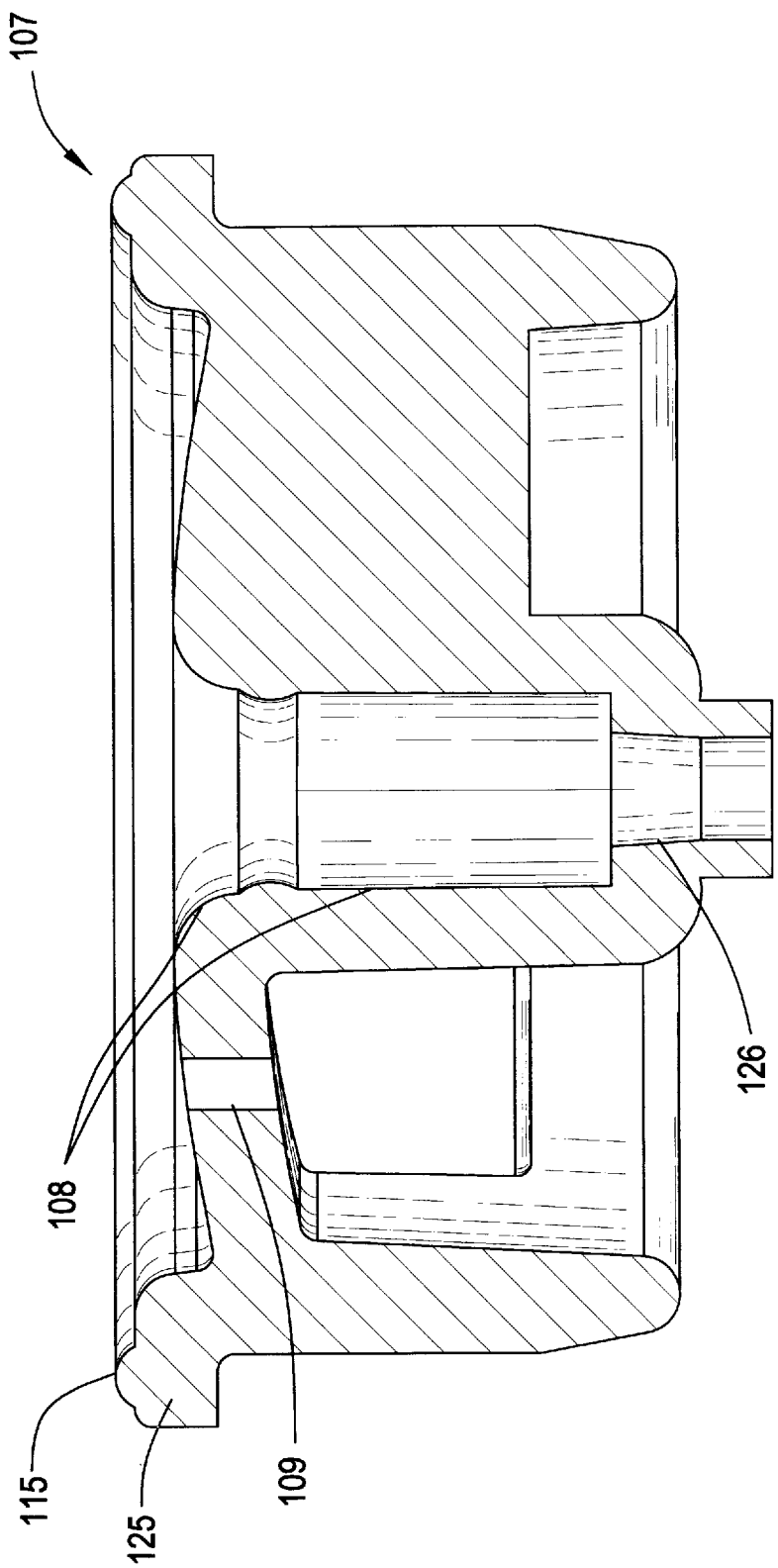
FIG. 7 illustrates a cross-section view of a permanent sealing assembly.

FIG. 7 illustrates an example cross-sectional view of a permanent sealing assembly 107. As illustrated, the permanent sealing assembly 107 includes a port 108, illustrated herein the form of a depression for accepting hollow nipple 116 of removable cap assembly 111. The permanent sealing assembly 107 includes a single vent aperture 109, although more than one vent aperture may be included. The vent aperture 109 is formed in the permanent sealing assembly 107 such that its upper surface resides in a cavity or depression formed in the permanent sealing assembly 107. This permits introduction of pressurized gas, e.g., from inflow tube 104, to be transmitted to an upper portion of the interior of a reagent bottle 101 and pressurization of the reagent bottle 101. The permanent sealing assembly 107 of FIG. 7 may be formed with a cavity therein such that less material (e.g., elastomeric material) is used. The permanent sealing assembly 107 may be molded to fit into a bottle 101 opening with an outcropping or perimeter portion 125 that prevents the permanent sealing assembly from falling into the interior of the bottle 101. The port 108 may, for its part, be fashioned such that it facilitates a sealing connection between the outflow tube 120 of the bottle 101 and the outflow tube 121 of an analysis instrument 110. In the example of FIG. 7, permanent sealing assembly 107 includes a tapered portion 126 of the port 108 at an interior end, i.e., facing the interior of the bottle 101. This permits the permanent sealing assembly 101 to interface at one end with the outflow tube 120 of the bottle 101, e.g., via insertion of the tapered portion 126 of the port into the outflow tube 120 of the bottle, with the upper portion of the port 108 being of larger diameter, e.g., for insertion of nipple 116.

Figure 8:
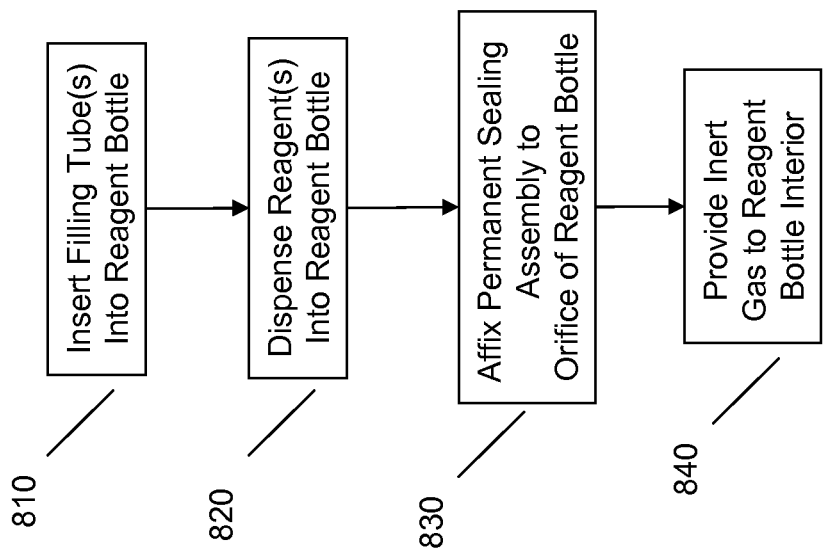
FIG. 8 illustrates an example reagent filling method.

Referring to FIG. 8, an example method of filling a reagent bottle 101 is illustrated. At 810 one or more filling tubes are inserted into a reagent bottle 101, e.g., via an orifice of the reagent bottle 101. The reagent(s) are then dispensed at 820 into the reagent bottle 101 to a predetermined amount. Thereafter a permanent sealing assembly 107 may be affixed to the reagent bottle 101 at 830, e.g., via ultrasonic welding, screwing in a threaded permanent sealing assembly 107, or the like. Depending on the nature of the reagent(s) in the reagent bottle 101, an inert gas such as argon may be provided to the interior of the reagent bottle 101 at 840 such that the reagents are protected from detrimental effects of atmospheric gases such as oxygen.

It should be noted that the steps outlined in FIG. 8 may be modified or altered to suit particular circumstances. For example, in the case of a re-filling operation, a reagent bottle 101 may first have its permanent sealing assembly 107 removed from the reagent bottle prior to filling. As another example, in the case of a permanent sealing assembly 107 comprising a septum, a new permanent sealing assembly 107 may be required. In a case where a septum is provided in permanent sealing assembly 107, the insertion of filling tube(s) may include piercing the septum to provide reagent filling and/or to provide vent aperture(s) 109 to the permanent sealing assembly 107. Moreover, the steps may have their orders altered, such as affixing a permanent sealing assembly 107 to an orifice of the reagent bottle 101 prior to inserting filling tube(s) into the bottle.

Figure 9:
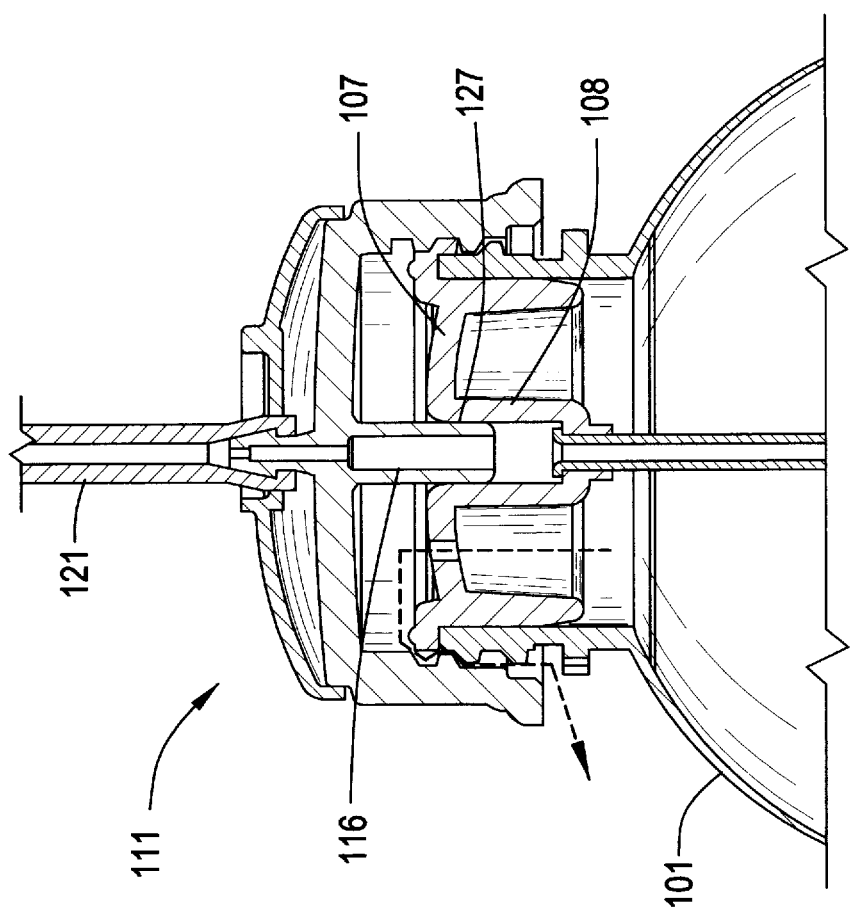
FIG. 9 illustrates a cross-section view of a permanent sealing assembly and removable cap assembly partially removed therefrom.

In FIG. 9 is illustrated a reagent bottle 101 having a removable cap assembly 111 partially removed. In the example illustrated in FIG. 9, the removable cap assembly 111 is partially unscrewed from the threaded orifice of the reagent bottle 101. In this position, hollow sealing nipple 116 is raised with respect to port 108 but its external circumference is still in sealing contact with sealing bead 127 thereby directing any pressure to be released through vent aperture 109 via the threads. This permits pressurized gas to be released (e.g., via pathway of dashed arrow in FIG. 9) such that the removal of removable cap assembly 111 from reagent bottle 101 is safer for a user, e.g., when removing a reagent bottle 101 from a system in a fault condition such as where reagent bottle 101 is pressurized. Moreover, the release of pressure prior to full removal of the removable cap assembly 111 from the reagent bottle 101 allows the reagent to remain within the interior of the reagent bottle 101, rather than being pushed out from the tube portion 120 of the reagent bottle 101 and forming a puddle or build up of reagent on the sealing assembly 107 top surface.

Therefore embodiments, by providing a reagent bottle 101 with an integrated tube or tube portion 120, the removal of a cap assembly 111 of a water analysis instrument 110 does not require the operator changing reagent bottles 101 to encounter a reagent wetted tube, e.g., tube 105 of a conventional cap assembly 103. Moreover, the removable cap assembly 111 may be safely placed aside while a new reagent bottle 101 is prepared (e.g., the temporary cap 112 is removed) without the need to worry that a tube portion extending from the removable cap assembly 111 to the interior of the reagent bottle will be contaminated by the surrounding environment. Therefore, embodiments provide an arrangement that reduces potential contact with reagent and potential contamination of the system.

This disclosure has been presented for purposes of illustration and description but is not intended to be exhaustive or limiting. Many modifications and variations will be apparent to those of ordinary skill in the art. The embodiments were chosen and described in order to explain principles and practical application, and to enable others of ordinary skill in the art to understand the disclosure for various embodiments with various modifications as are suited to the particular use contemplated.

Although illustrative embodiments have been described herein, including the non-limiting examples provided in Appendix A and Appendix B, each of which form part of this description, and illustrated in the figures, it is to be understood that the embodiments are not limited to those precise example embodiments, and that various other changes and modifications may be affected therein by one skilled in the art without departing from the scope or spirit of the disclosure.

LIST OF REFERENCE NUMERALS

101—Reagent Bottle
103—Cap Assembly
104—Inflow Tube
105—Outflow Tube

106—Filter Assembly
107—Seal Assembly
108—Port
109—Vent Aperture
110—Analysis Instrument
111—Removable Cap Assembly
112—Temporary Cap
113—Sealing Nipple
115—Sealing Bead
116—Hollow Sealing Nipple
117—Elastomeric Stopper Body
120—Tube Portion
121—Outflow Tube
125—Perimeter Portion
126—Tapered Portion
127—Sealing Bead

What is claimed is:

1. A removable cap assembly comprising:
an outer portion that attaches to an orifice of a container through a plurality of threads defined in an inner surface of the outer portion of the removable cap assembly;
wherein the inner surface of the outer portion of the removable cap assembly defines a cavity in an underside of the outer portion, wherein the cavity in the underside of the outer portion provides a gap between the underside of the outer portion of the removable cap assembly and a top of a permanent sealing assembly disposed in the container to which the removable cap assembly attaches;
a connecting portion that, when the outer portion of the removable cap assembly is secured to the orifice of the container, contacts and seals with an outflow tube portion of the permanent sealing assembly of the container, wherein the connecting portion comprises a nipple that extends outwardly from an underside of the removable cap assembly;
an inflow tube that provides inflow of gas to provide positive pressure to the container interior; and
an outflow tube extending between a liquid analysis instrument and the connecting portion that provides outflow of contents of the container via fluid communication between the nipple and the outflow tube of the permanent sealing assembly of the container;
wherein, in response to the removable cap assembly being partially unscrewed, a plurality of threads of an outer surface of the orifice and the plurality of threads of the removable cap assembly form a vent region.

2. The removable cap assembly of claim 1, wherein the inflow tube terminates at the removable cap assembly and does not extend appreciably into an interior of the container.

3. The removable cap assembly of claim 2, wherein the inflow tube does not contact any portion of the container.

4. The removable cap assembly of claim 1, wherein the plurality of threads compliments a plurality of threads of the orifice of the container.

5. A system, comprising:
a liquid analysis instrument comprising a microprocessor in electrical communication with valves and a gas manifold; and
a removable cap assembly comprising:
an outer portion that attaches to an orifice of a container through a plurality of threads defined in an inner surface of the outer portion of the removable cap assembly;
wherein the inner surface of the outer portion of the removable cap assembly defines a cavity in an underside of the outer portion, wherein the cavity in the underside of the outer portion provides a gap between the underside of the outer portion of the removable cap assembly and a top of a permanent sealing assembly disposed in the container to which the removable cap assembly attaches;
a connecting portion that, when the outer portion of the removable cap assembly is secured to the orifice of the bottle, contacts and seals with an outflow tube portion of the permanent sealing assembly of the container, wherein the connecting portion comprises a nipple that extends outwardly from an underside of the removable cap assembly;
wherein, in response to the removable cap assembly being partially unscrewed, a plurality of threads of an outer surface of the orifice and the plurality of threads of the removable cap assembly form a vent region;
an inflow tube that provides inflow of gas from the liquid analysis instrument to provide positive pressure to the container interior; and
an outflow tube extending between the liquid analysis instrument and the connecting portion that provides outflow of contents of the container to the liquid analysis instrument via fluid communication between the nipple and the outflow tube of the permanent sealing assembly of the container.

6. The system of claim 5, wherein the inflow tube terminates at the removable cap assembly and does not extend appreciably into an interior of the container.

7. The system of claim 6, wherein the inflow tube does not contact any portion of the container.

8. The system of claim 5, wherein the plurality of threads compliments a plurality of threads of the orifice of the container.

9. The system of claim 5, further comprising the container.

* * * * *